(12) United States Patent
Uskokovic

(10) Patent No.: US 6,559,138 B1
(45) Date of Patent: May 6, 2003

(54) 3-DESOXY-VITAMIN D₃ ANALOG ESTERS

(75) Inventor: Milan Radoje Uskokovic, Upper Montclair, NJ (US)

(73) Assignee: Syntex (U.S.A.) LLC, Palo Alto, CA (US)

( * ) Notice: Subject to any disclaimer, the term of this patent is extended or adjusted under 35 U.S.C. 154(b) by 0 days.

(21) Appl. No.: 10/246,333

(22) Filed: Sep. 18, 2002

Related U.S. Application Data

(60) Provisional application No. 60/323,957, filed on Sep. 21, 2001.

(51) Int. Cl.⁷ .................. A61K 31/593; C07C 401/00
(52) U.S. Cl. ........................ 514/167; 552/653
(58) Field of Search ............... 552/653; 514/167

(56) References Cited

U.S. PATENT DOCUMENTS

| | | | | |
|---|---|---|---|---|
| 5,939,408 A | * | 8/1999 | Batcho et al. | 514/167 |
| 6,043,386 A | * | 3/2000 | Posner et al. | 552/653 |
| 6,184,398 B1 | * | 2/2001 | Kawase et al. | 552/653 |
| 6,380,408 B1 | * | 4/2002 | Posner et al. | 552/653 |

OTHER PUBLICATIONS

Alex j. Brown et al., Kidney International, vol. 38, Suppl. 29 (1990), S–22–S–27.*

Koike et al., "20–Cyclopropyl–cholecalciferol Vitamin D3 Analogs," *Anticancer Research*, (1999) pp 1689–1697, vol. 19:(3A).

Uskokovic et al., "The 16–ene Analogs of 1,25–Dihydroxy-cholecalciferol. Synthesis and Biological Activity," (1991) pp 139–145 from *Proceedings of the Eighth Workshop on Vitamin D*, Paris, France.

* cited by examiner

Primary Examiner—Sabiha Qazi
(74) Attorney, Agent, or Firm—Rohan Peries

(57) ABSTRACT

The present invention provides 3-desoxy vitamin D₃ analog esters of the formula:

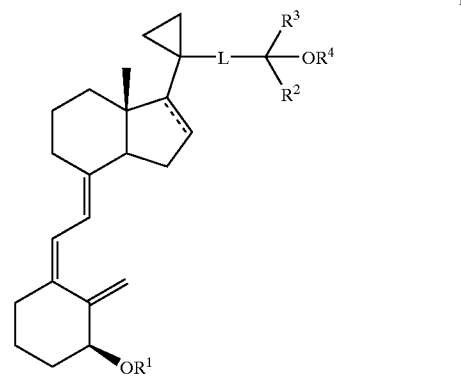

and methods for use and preparation of the same, wherein the dotted line, $R^1$, $R^2$, $R^3$, $R^4$ and L are those defined herein.

19 Claims, No Drawings

3-DESOXY-VITAMIN $D_3$ ANALOG ESTERS

CROSS-REFERENCE

This application claims the benefit of priority of U.S. Provisional Patent Application Serial No. 60/323,957, filed Sep. 21, 2001, which is incorporated herein by reference in its entirety.

FIELD OF THE INVENTION

This invention relates to 3-desoxy-20-desmethyl-20-cyclopropyl vitamin $D_3$ analog esters and methods for producing and using the same.

BACKGROUND OF THE INVENTION

Osteoporosis

Osteoporosis is the most common form of metabolic bone disease and may be considered the symptomatic, fracture stage of bone loss (osteopenia). Although osteoporosis may occur secondary to a number of underlying diseases, 90% of all cases appear to be idiopathic. Postmenopausal women are at risk for idiopathic osteoporosis (postmenopausal or Type I osteoporosis); another particularly high risk group for idiopathic osteoporosis is the elderly of either sex (senile or Type II osteoporosis). Osteoporosis has also been related to corticosteroid use, immobilization or extended bed rest, alcoholism, diabetes, gonadotoxic chemo-therapy, hyperprolactinemia, anorexia nervosa, primary and secondary amenorrhea, transplant immunosuppression, and oophorectomy. Postmenopausal osteoporosis is characterized by fractures of the spine, while femoral neck fractures are the dominant features of senile osteoporosis.

The mechanism by which bone is lost in osteoporotics is believed to involve an imbalance in the process by which the skeleton renews itself. This process has been termed bone remodeling. It occurs in a series of discrete pockets of activity. These pockets appear spontaneously within the bone matrix on a given bone surface; as a site of bone resorption. Osteoclasts (bone dissolving or resorbing cells) are responsible for the resorption of a portion of bone of generally constant dimension. This resorption process is followed by the appearance of osteoblasts (bone forming cells) which then refill with new bone the cavity left by the osteoclasts.

In a healthy adult subject, osteoclasts and osteoblasts function so that bone formation and bone resorption are in balance. However, in osteoporotics an imbalance in the bone remodeling process develops which results in bone being replaced at a slower rate than it is being lost. Although this imbalance occurs to some extent in most individuals as they age, it is much more severe and occurs at a younger age in postmenopausal osteoporotics, following oophorectomy, or in iatrogenic situations such as those resulting from corticosteroid therapy or the immunosuppression practiced in organ transplantation.

Various approaches have been suggested for increasing bone mass in humans afflicted with osteoporosis, including administration of androgens, fluoride salts, and parathyroid hormone and modified versions of parathyroid hormone. It has also been suggested that bisphosphonates, calcitonin, calcium, 1,25-dihydroxy vitamin $D_3$ and some of its analogs, and/or estrogens, alone or in combination, may be useful for preserving existing bone mass.

Vitamin $D_3$ is a critical element in the metabolism of calcium, promoting intestinal absorption of calcium and phosphorus, maintaining adequate serum levels of calcium and phosphorus, and stimulating flux of calcium into and out of bone. Vitamin $D_3$ is hydroxylated in vivo, with the resulting 1α,25-dihydroxy metabolite being the active material. Animal studies with 1,25-$(OH)_2$ vitamin $D_3$ have suggested bone anabolic activity. Aerssens et al. in *Calcif Tissue Int*, 55:443–450 (1994) reported upon the effect of 1α-hydroxy Vitamin $D_3$ on bone strength and composition in growing rats with and without corticosteroid treatment. However, human usage is restricted to antiresorption due to the poor therapeutic ratio (hypercalciuria and hypercalcemia as well as nephrotoxicity).

Dechant and Goa, in "Calcitriol. A review of its use in the treatment of postmenopausal osteoporosis and its potential in corticosteroid-induced osteoporosis," Drugs Aging [NEW ZEALAND 5 (4): 300–17 (1994)], reported that 1,25-dihydroxyvitamin $D_3$ (calcitriol) has shown efficacy in the treatment of postmenopausal osteoporosis (and promise in corticosteroid-induced osteoporosis) based upon a clinical trial in 622 women with postmenopausal osteoporosis. Patients with mild to moderate disease (but not those with more severe disease) who received calcitriol (0.25 microgram twice daily) had a significant 3-fold lower rate of new vertebral fractures after 3 years of treatment compared with patients receiving elemental calcium 1000 mg/day. In patients commencing long term treatment with prednisone or prednisolone, calcitriol 0.5 to 1.0 micrograms/day plus calcium 1000 mg/day, administered with or without intranasal calcitonin 400 IU/day, prevented steroid-induced bone loss. Overall, calcitriol was well tolerated. At recommended dosages hypercalcaemia was infrequent and mild, generally responding to reductions in calcium intake and/or calcitriol dosage. However, the narrow therapeutic window of calcitriol required that its use be adequately supervised, with periodic monitoring of serum calcium and creatinine levels. This study clearly identifies the key limitation of calcitriol therapy as the close proximity of therapeutic and toxic doses.

Certain 3-desoxy-20-cyclopropyl vitamin D3 analogs are disclosed as inhibiting cellular proliferation in vitro in prostate cancer lines ("20-Cyclopropyl-Cholecalciferol Vitamin D3 Analogs," M. Koike et. al., *Anticancer Research*, 19:1689–1698 (1999))

Hyperparathyroidism

Secondary hyperparathyroidism is a common finding in patients with chronic renal failure. It is established that the reduction of renal 1,25$(OH)_2$ vitamin $D_3$ (calcitriol) synthesis is one of the principal mechanisms leading to the secondary hyperparathyroidism in these patients and it has been shown that calcitriol possesses direct suppressive action on PTH synthesis. Therefore, administration of calcitriol has been recommended for the treatment of secondary hyperparathyroidism in these patients. However, as described above, calcitriol has potent hypercalcemic effects giving it a narrow therapeutic window which limits its usage, especially at high doses. It would therefore be desirable to have an alternative means of treating hyperparathyroidism without incurring these undesirable hypercalcemic effects.

While a variety of compounds are available for treating these and other diseases, many of these compounds have undesirable side-effects and/or are relatively unstable, i.e., have short storage period. Therefore, there is a continuing needs for other compounds which are useful in treating these diseases.

BRIEF SUMMARY OF THE INVENTION

One aspect of the present invention provides a 3-desoxy vitamin $D_3$ analog ester of the formula:

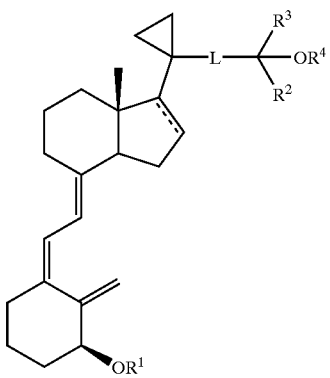

I or a salt thereof, and methods for using and producing the same, where dotted line is optionally a double bond;

L is a linker selected from the group consisting of:
—$CH_2$—$CH_2$—$CH_2$—,
—$CH_2$—CH=CH—,
—$CH_2$—C≡C—,
—$CH_2$—$CH_2$—C(=O)—, and
—CH=CH—CH=CH—;

each of $R^2$ and $R^3$ is independently alkyl or haloalkyl; or $R^2$ and $R^3$ and together with the carbon atom to which they are attached to form a cycloalkyl; and each of $R^1$ and $R^4$ is independently hydrogen, alkyl, acyl group or other hydroxy protecting group, provided at least one of $R^1$ and $R^4$ is an acyl group.

DEFINITIONS

"Acetate" or "Ac" are used interchangeably herein and refer to a moiety of the formula —C(=O)$CH_3$.

"Acyl" refers to a moiety of the formula —C(O)R', where R' is alkyl, heteroalkyl, cycloalkyl, aryl, heteroaryl, aralkyl or heteroaralkyl.

"Alkyl" means a linear fully-saturated hydrocarbon moiety having one to six, preferably one to four, carbon atoms or a branched fully saturated hydrocarbon moiety having three or six carbon atoms.

"Aralkyl" means a moiety of the formula —$R^a$—$R^b$, where $R^a$ is alkyl and $R^b$ is aryl as defined herein.

"Aryl" means a monocyclic or bicyclic aromatic hydrocarbon moiety. In addition, one or more, preferably one, two or three, hydrogen atoms of the aryl moiety can be replaced by halo, nitro, cyano, hydroxy, amino, alkyl or alkoxy. Exemplary aryl groups include phenyl and naphthalenyl which can be substituted with one or more substituents listed above. Preferably, aryl is phenyl.

"Cycloalkyl" means a fully saturated cyclic hydrocarbon moiety of three to six ring carbon atoms, e.g., cyclopropyl, cyclopentyl and the like.

"Ester" refers to a compound comprising a moiety of the formula —O—C(=O)—R', where R' is alkyl, heteroalkyl, cycloalkyl, aryl, heteroaryl, aralkyl or heteroaralkyl.

"Haloalkyl" refers to an alkyl moiety, as defined above, in which one or more hydrogen atoms attached to the carbon backbone have been replaced with one or more halides. Preferred halide is fluoride.

"Heteroalkyl" means an alkyl moiety as defined herein having one or more, preferably one, two or three, substituents selected from —$NR^aR^b$, —$OR^c$ wherein $R^a$, $R^b$ and $R^c$ are independently of each other hydrogen, alkyl, or the corresponding protecting group.

"Heteroaralkyl" means a moiety of the formula —$R^a$—$R^b$, where $R^a$ is alkyl and $R^b$ is heteroaryl as defined herein.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. In addition, one or more, preferably one, two or three, hydrogen atoms of the heteroaryl moiety can be replaced by the substituents described above for the aryl group.

The terms "hydroxy protecting group" and "other hydroxy protecting group" are used interchangeably herein and refer to hydroxy protecting groups known to one skilled in the art excluding alkyl or acyl groups, which are referred herein specifically. Representative hydroxy protecting groups include silyl ethers, carbonates, carbamates, substituted methyl ethers, substituted ethyl ethers, and the like. A list of other suitable hydroxy protecting groups can be found, for example, in *Protective Groups in Organic Synthesis*, 3rd edition, T. W. Greene and P. G. M. Wuts, John Wiley & Sons, New York, 1999, which is incorporated herein by reference in its entirety.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. "A pharmaceutically acceptable excipient" as used in the specification and claims includes both one and more than one such excipient.

"Therapeutically effective amount" means the amount of a compound that, when administered to a mammal for treating or preventing a disease, is sufficient to effect such treatment or prevention for the disease. The "therapeutically effective amount" will vary depending on the compound, the disease and its severity and the age, weight, etc., of the patient to be treated.

"Treating" or "treatment" of a disease includes: (1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

When referring to a chemical reaction, the terms "treating", "contacting" and "reacting" are used interchangeably herein and refer to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as preferred, more preferred and most preferred definitions, if any.

DETAILED DESCRIPTION

One aspect of the present invention provides a 3-desoxy-20-desmethyl-20-cyclopropyl vitamin $D_3$ analog ester of the formula:

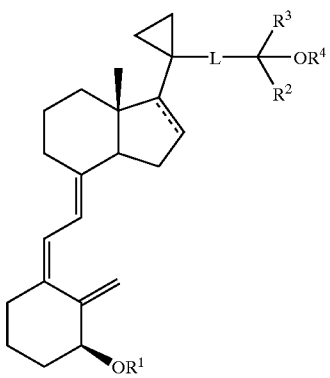

I or a salt thereof, wherein dotted line is optionally a double bond;

L is a linker selected from the group consisting of:
—$CH_2$—$CH_2$—$CH_2$—,
—$CH_2$—CH=CH—,
—$CH_2$—C≡C—,
—$CH_2$—$CH_2$—C(=O)—, and
—CH=CH—CH=CH—;

each of $R^2$ and $R^3$ is independently alkyl or haloalkyl; or $R^2$ and $R^3$ and together with the carbon atom to which they are attached to form a cycloalkyl; and each of $R^1$ and $R^4$ is independently hydrogen, alkyl, acyl group or other hydroxy protecting group, provided at least one of $R^1$ and $R^4$ is an acyl group.

It has been surprisingly discovered that compounds of Formula I, where at least one of $R^1$ and $R^4$ is an acyl group are unexpectedly stable and crystalline relative to the compound where both of $R^1$ and $R^4$ are hydrogen, i.e., the parent diol.

When the cyclopentane ring moiety of Formula I does not contain a double bond, i.e., when the dotted line is absent, the stereochemistry of the side chain on the cyclopentane ring system can be alpha or beta. Preferably, the stereochemistry of the side chain on the cyclopentane ring system is beta, i.e., of the formula:

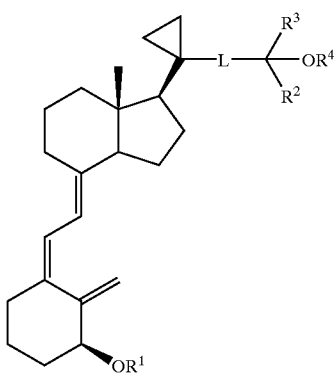

In one particular embodiment of the present invention, the 3-desoxy vitamin $D_3$ analog ester is of the formula:

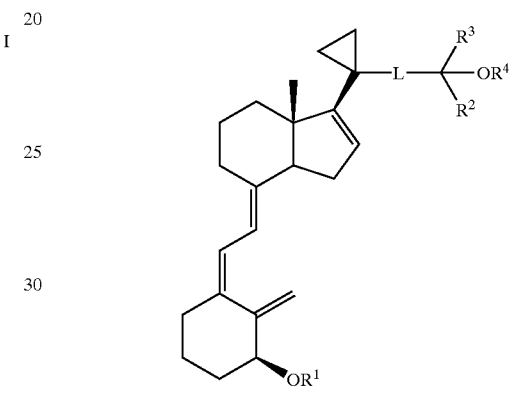

where $R^1$, $R^2$, $R^3$, $R^4$ and L are those defined herein.

In still another embodiment, the linker L is selected from the group consisting of —$CH_2$—$CH_2$—$CH_2$—; —$CH_2$—CH=CH—; —$CH_2$—C≡C—; and, —CH=CH—CH=CH—. Preferably, L is —$CH_2$—CH=CH— or —$CH_2$—C≡C—. More preferably L is —$CH_2$—CH=CH— where the double bond is trans.

Yet in another embodiment, $R^1$ is preferably an acyl group, more preferably acetyl.

Still in another embodiment, $R^1$ is an acyl group and $R^4$ is hydrogen or an acyl group.

In another embodiment, $R^1$ is an acyl group and each of $R^2$ and $R^3$ is independently selected from the group consisting of methyl, ethyl and trifluoromethyl.

In yet another embodiment, $R^2$ and $R^3$ are alkyl or haloalkyl, preferably methyl or trifluoromethyl, most preferably trifluoromethyl.

A number of different substituent preferences have been given above and following any of these substituent preferences results in a compound of the invention that is more preferred than one in which the particular substituent preference is not followed. However, these substituent preferences are generally independent, although some preferences are mutually exclusive, and following more than one of these preferences may result in a more preferred compound than one in which fewer of the substituent preferences are followed.

| Compound | Structure | Melting Point | Mass Spec M+ |
|---|---|---|---|
| 1 | 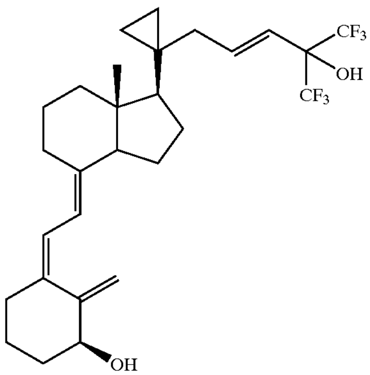 | | 535(M + H) |
| 2 | 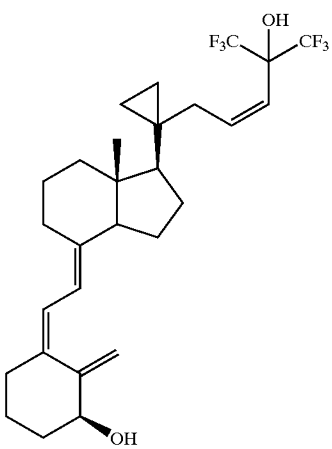 | | 518 |
| 3 | 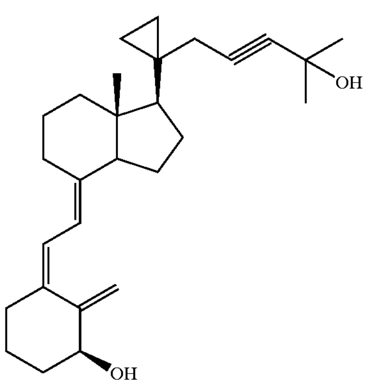 | | 408.3 |

Selected Compounds of the Invention

-continued

Selected Compounds of the Invention

| Compound | Structure | Melting Point | Mass Spec M+ |
|---|---|---|---|
| 4 | 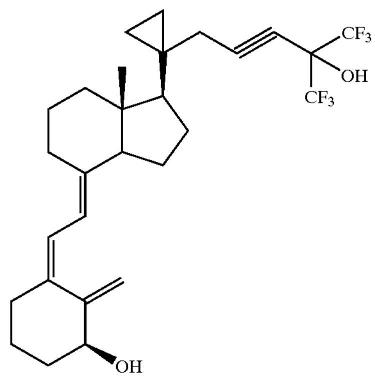 | | 516 |
| 5 | 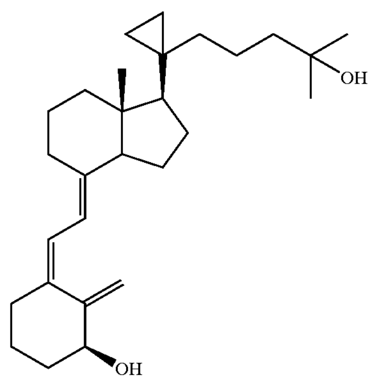 | | |
| 6 | 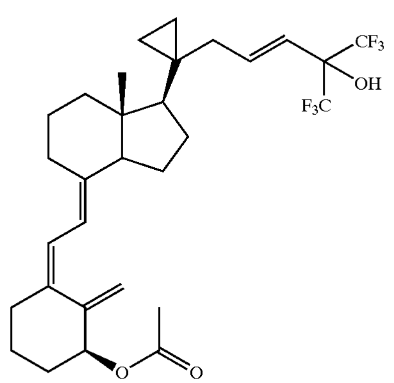 | | |

-continued

Selected Compounds of the Invention

| Compound | Structure | Melting Point | Mass Spec M+ |
|---|---|---|---|
| 7 | 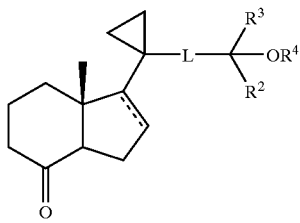 | | |

General Synthetic Scheme

While a variety of synthetic methodologies are available for preparation of compounds of Formula I, one particular embodiment for preparing compounds of Formula I includes coupling a ketone with a phosphine oxide. Specifically, compounds of Formula I can be prepared by contacting a compound of Formula II,

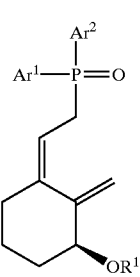

II with a phosphine oxide compound of the formula:

$$Ar^1\!-\!\!\underset{\underset{O}{\parallel}}{P}\!-\!Ar^2$$

III (phosphine oxide structure with OR¹ group)

under conditions sufficient to produce the compound of Formula I, wherein
each of $Ar^1$ and $Ar^2$ is independently optionally substituted aryl;
dotted line is optionally a double bond;
L is a linker selected from the group consisting of:
—$CH_2$—$CH_2$—$CH_2$—,
—$CH_2$—CH=CH—,
—$CH_2$—C≡C—,
—$CH_2$—$CH_2$—C(=O)—, and
—CH=CH—CH=CH—;
each of $R^2$ and $R^3$ is independently alkyl or haloalkyl; or $R^2$ and $R^3$ and together with the carbon atom to which they are attached to form a cycloalkyl; and
each of $R^1$ and $R^4$ is independently alkyl, an acyl group or a hydroxy protecting group, and (b) when neither $R^1$ nor $R^4$ is an acyl group, acylating the compound of Formula I with an acylating agent under conditions sufficient to produce a Compound of Formula I where at least one of $R^1$ and $R^4$ is an acyl group.

In one embodiment, $R^1$ and $R^4$ are hydroxy protecting groups. In this particular embodiment, the acylating step (b) comprises:

(i) removing the hydroxy groups by contacting the resulting compound of said step (a) with a hydroxy protecting group removing compound under conditions sufficient to produce a 1-hydroxy-3-desoxy vitamin $D_3$ analog of the formula:

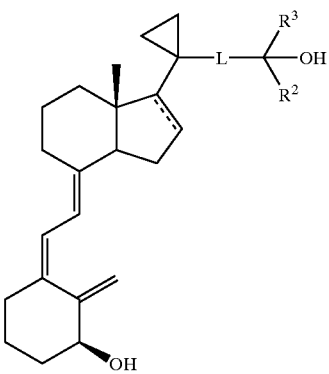

and (ii) contacting the 1-hydroxy-3-desoxy vitamin $D_3$ analog with an acylating agent under conditions sufficient to produce a 3-desoxy vitamin $D_3$ analog ester of the Formula:

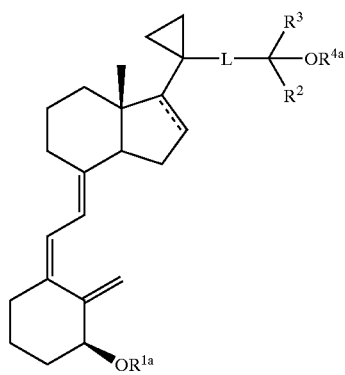

wherein $R^{1a}$ is an acyl group and $R^{4a}$ is hydrogen or an acyl group.

In another embodiment, $R^{4a}$ is an acyl group.

In yet another embodiment, $Ar^1$ and $Ar^2$ are phenyl.

Suitably hydroxy protecting groups are well known to one of ordinary skill in the art and examples of such hydroxy protecting groups are disclosed in *Protective Groups in Organic Synthesis*, 3rd edition, T. W. Greene and P. G. M. Wuts, John Wiley & Sons, New York, 1999, and Harrison and Harrison et al., *Compendium of Synthetic Organic Methods*, Vols. 1–8 (John Wiley and Sons, 1971–1996), which are incorporated herein by reference in their entirety. Representative hydroxy protecting groups include benzyl and trityl ethers, tetrahydropyranyl ethers, trialkylsilyl ethers, carbamates and allyl ethers.

Typically, hydroxy groups are protected as silyl ethers; however, the scope of the invention includes the use of alternative hydroxyl protecting groups known in the art as described in the above disclosed *Protective Groups in Organic Synthesis*, 3rd edition, and *Compendium of Synthetic Organic Methods*, Vols. 1–8.

In general, a phosphine oxide of Formula III in tetrahydrofuran is reacted with n-butyllithium typically at about −78° C. To this mixture is then added solution of a ketone of Formula II in tetrahydrofuran to provide a compound of Formula I. As stated above, when $R^1$ and/or $R^4$ are hydrogen, they are protected with hydroxy protecting groups prior to the coupling reaction. In such a case, the hydroxy protecting groups are then removed to provide a compound of Formula I.

Synthesis and purification of compounds of Formula III are known and conventional in this art. See, for example, M. R. Uskokovic et al. "Vitamin D Gene Regulation, Structure Function Analysis and Clinical Application," Paris, France, pp 139–145 (1991), U.S. Pat. No. 5,086,191 and U.S. Pat. No. 5,616,759 to DeLuca et al., U.S. Pat. No. 5,087,619 to Baggiolini et al., U.S. Pat. No. 5,384,314 to Doran et al., U.S. Pat. No. 5,428,029 to Doran et al., U.S. Pat. No. 5,451,574 to Baggiolini et al.; European patent publication EP 0 808,832 A2, patent publication WO 96/31216 to Brasitus et al.; Shiuey et al., *J. Org. Chem.*, 55:243–247 (1990), Kiegel, J. et al. and *Tetr. Lett.*, 32:6057–6060 (1991), Perlman, K. L., et al., *Tetr. Lett.*, 32:7663–7666 (1991).

Reaction Scheme 1 illustrates a synthetic method for preparing a compound of Formula IA.

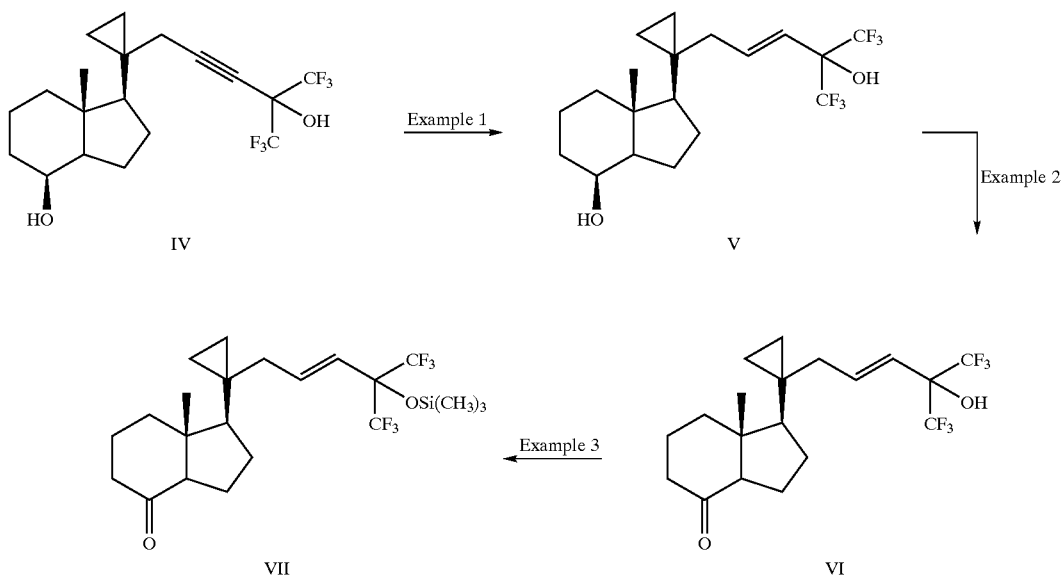

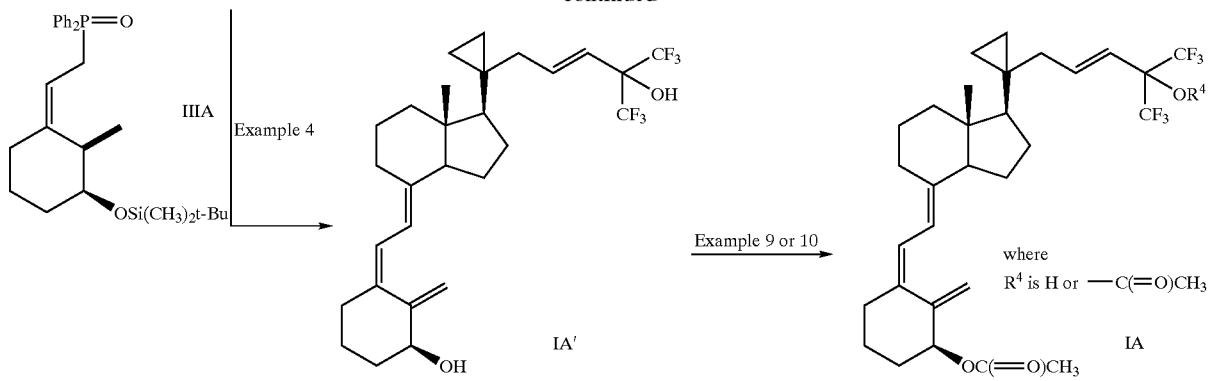

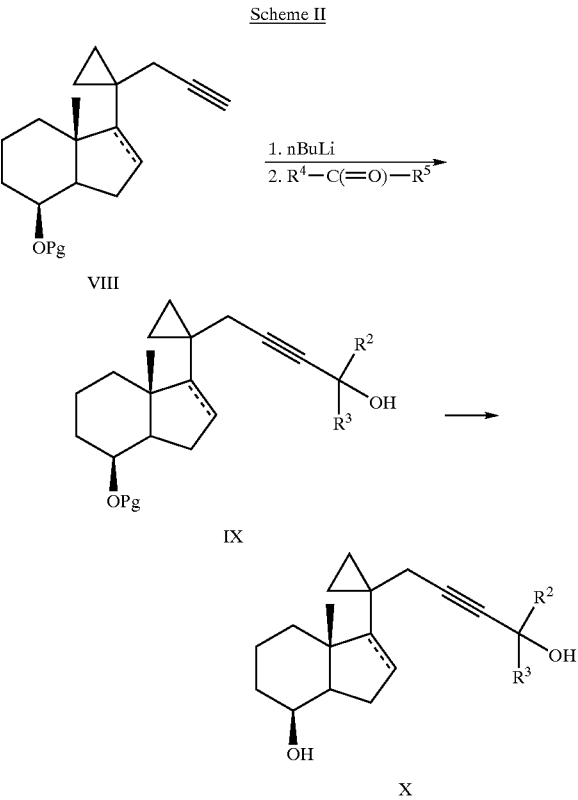

In Reaction Scheme 1, the compound of Formula IV is a known compound prepared by the method described in W099/12894, published Mar. 18, 1999 (Preparation of 1,3-dihydroxy-20,20-dialkyl vitamin D3 analogs). The compound of Formula IV is converted to the compound of Formula V by selective partial reduction of the triple bond to an b E-double bond using lithium aluminum hydride in inert organic acid such as tetrahydrofuran. The reaction is typically conducted by adding the compound of Formula IV to a suspension of $LiAlH_4$ in THF at 0° C. or 5° C. The reaction mixture is heated under refluxing condition to provide the compound of Formula V. The compound of Formula V is converted to the ketone of Formula VI by oxidation using an oxidizing agent such as pyridinium dichromate. The reaction is generally conducted in a halogenated solvent such as methylene chloride at room temperature. The hydroxy group of compound of Formula VI is then protected as a: silyl ether of Formula VII using a silylating agent, such as 1-(trimethylsilyl)imidazole, trimethylsilyl chloride or trimethylsilyl triflate, in an inert solvent, such as a halogenated solvent (e.g., methylene chloride), at room temperature. The compound of Formula IIIA is reacted with n-butyllithium and the resulting compound is reacted with the compound of Formula VII in tetrahydrofuran at temperature of generally about −78° C., and the silyl protecting groups are then removed, for example, with tetrabutylammonium fluoride in tetrahydrofuran solvent to give the compound of Formula IA'. The free hydroxyl groups are then acetylated to provide the compound of Formula IA, for example, with acetic anhydride in pyridine. Because the secondary hydroxyl group is generally more reactive, it can be selectively acetylated depending on the amount of acetylating agent used and/or the reaction conditions used, e.g., the reaction temperature and/or the reaction time. Alternatively, both the secondary and the tertiary hydroxyl groups can be aceytlated by using an excess amount of the acetylating agent and longer reaction time.

Similarly, a Z-stereoisomer analog or a saturated carbon chain analog of compound of Formula IA can be prepared by reduction of the compound of Formula IV with hydrogen in the presence of an appropriate hydrogenation catalyst, such as Pd—S or Pd, respectively. The resulting compounds can be subjected to similar reaction conditions as shown in Scheme I to produce the corresponding a Z-isomer analog and a saturated carbon chain analog of the compound of Formula IA.

As shown in Reaction Scheme II, a compound of Formula II comprising an acetylenic alcohol and varying alkyl, haloalkyl and cycloalkyl groups of $R^2$ and $R^3$ can be prepared by condensing an acetylide anion derived from a compound of Formula VIII (where Pg is a hydroxy protecting group) with an appropriate ketone, haloketone (e.g. hexafluoroacetone) and cycloketone, and removing the protecting group.

The compound of Formula X is then subjected to a similar reaction conditions shown above in Reaction Scheme I (i.e., oxidation, protection and coupling) to produce a compound of Formula I having an acetylenic linker moiety.

Preferred Embodiments

In certain preferred embodiments, the dotted line is a double bond, i.e., a compound of the formula:

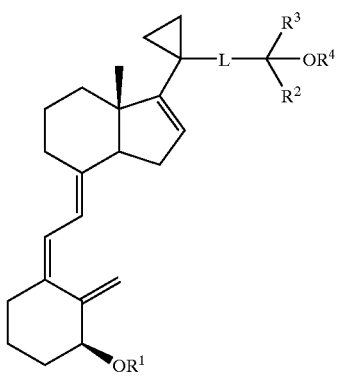

In yet another preferred embodiment, the linker L is selected from the group consisting of:

—CH$_2$—CH$_2$—CH$_2$—;
—CH$_2$—CH=CH—;
—CH$_2$—C≡C—; and
—CH=CH—CH=CH—.

Preferably, R$^1$ is an acyl group.
Preferably, R$^4$ is hydrogen or an acyl group.
Preferably, each of R$^2$ and R$^3$ is independently selected from the group consisting of methyl, ethyl and trifluoromethyl or R$^2$ and R$^3$ together with the carbon atom to which they are attached to form a cyclopentyl ring.

A number of different substituent preferences have been given above and following any of these substituent preferences results in a compound of the invention that is more preferred than one in which the particular substituent preference, is not followed. However, these substituent preferences are generally independent, although some preferences are mutually exclusive, and following more than one of these preferences may result in a more preferred compound than one in which fewer of the substituent preferences are followed.

Another aspect of the invention provides salts of a compound of Formula I.

Utility

The compounds of the present invention are useful for the prevention and treatment of a variety of mammalian conditions manifested by loss of bone mass. All such conditions are referred to as "bone-related diseases" and are described in more detail hereunder. In particular, the compounds of this invention are indicated for the prophylaxis and therapeutic treatment of osteoporosis and osteopenia in mammals without inducing hypercalciuria, hypercalcemia, or nephrotoxicity. "Hypercalcemia" is an excessive concentration of calcium in the serum; in humans (and rats) this corresponds to greater than about 10.5 mg/dl. "Intolerable hypercalcemia", usually occurring at serum calcium concentrations greater than about 12 mg/dl, is associated with emotional lability, confusion, delirium, psychosis, stupor, and coma.

The compounds of the present invention are useful in the treatment of Type I (postmenopausal), Type II (iatrogenic), and Type III (senile) osteoporosis, including that associated with corticosteroid treatment (e.g. for asthma), as well in the treatment of osteodystrophy due to renal dialysis and hyperparathyroidism. Treatment with the vitamin D3 analogs as described herein results in increased bone mineral density and unlike conventional treatments provides bone of good quality. Therefore, the treatments described herein may reduce the incidence of fracture and result in faster healing of pre-existing fractures. Such treatments are particularly useful for patients suffering from estrogen withdrawal (e.g. elderly females) who would otherwise be at risk for an increased fracture rate. Types of fractures treatable include both traumatic and osteoporotic fractures, e.g., fractures of the hip, neck of the femur, wrist, vertebrae, spine, ribs, sternum, larynx and trachea, radius/ulna, tibia, patella, clavicle, pelvis, humerus, lower leg, fingers and toes, face and ankle.

The compounds of the present invention are also useful in treating diseases caused by elevated levels of parathyroid hormone. In one aspect, compounds of the invention are used in treating secondary hyperparathyroidism associated with renal failure and in particular with reversing or reducing the bone loss associated with renal insufficiency. Other aspects include the treatment of renal osteodystrophy associated with late stage secondary hyperparathyroidism. Other aspects include the treatment of primary hyperparathyroidism.

Compounds of Formula I are also useful in treating neoplastic diseases such as leukemia, colon cancer, breast cancer and prostate cancer.

Generally, compounds of the present invention do not cause the elevated calcium levels observed with other vitamin D$_3$ analogs such as 1,25 (OH)$_2$ vitamin D$_3$, thus providing an improved therapeutic ratio and better treatment of the above diseases.

Administration & Pharmaceutical Compositions

In general, the compound of this invention may be administered in amounts between about 0.0002 and 0.5 mg compound/kg body weight per day, preferably from about 0.001 to about 0.1 mg/kg body weight per day, more preferably from about 0.002 to about 0.02 mg/kg body weight per day, most preferably from about 0.005 to about 0.010 mg/kg body weight per day. For a 50 kg human subject, the daily dose of active ingredient may be from about 0.01 to about 25 μgs, preferably from about 0.05 to about 10 μgs, most preferably from about 1.0 μg to about 10 μg per day. This dosage can be delivered in a conventional pharmaceutical composition by a single administration, by multiple applications, or via controlled release, as needed to achieve the most effective results, preferably once or twice daily by mouth. In certain situations, alternate day dosing can prove adequate to achieve the desired therapeutic response.

The selection of the exact dose and composition and the most appropriate delivery regimen are influenced by, inter alia, the pharmacological properties of the formulation, the nature and severity of the condition being treated, and the physical condition and mental acuity of the recipient. In general, the requisite dose is greater for higher doses of corticosteroids in the treatment of corticosteroid induced osteopenia.

Representative delivery regimens include oral,; parenteral (including subcutaneous, intramuscular and intravenous), rectal, buccal (including sublingual), pulmonary, transdermal, and intranasal, most preferably oral. Administration can be continuous or intermittent (e.g., by bolus injection).

A related aspect of this invention relates to combination therapies of compounds of Formula I with other active agents such as bisphosphonates, estrogen, SERMS (selective estrogen receptor modulators), calcitonins or anabolic therapies. Examples of bisphosphonates include alendronate, ibandronate, pamidronate, etidronate and risedronate. Examples of SERMS include raloxifene, dihydroraloxifene and lasofoxifene. Calcitonins include human and salmon calcitonin. Anabolic agents include parathyroid hormones (PTH) e.g. hPTH(1–34), PTH(1–84), and parathyroid hormone-related protein (PTHrP) and analogs thereof. Particular analogs of PTHrP are described in "Mono- and Bicyclic Analogs of Parathyroid Hormone-Related Protein. 1. Synthesis and Biological Studies," Michael Chorev et al. Biochemistry, 36:3293–3299 (1997) and "Cyclic analogs of PTH and PTHrP," WO 96/40193 and U.S. Pat. No. 5,589,452 and WO 97/07815. The other active agent may be administered concurrently, prior to or after the compound of Formula I and may be administered by a different delivery method.

A further aspect of the present invention relates to pharmaceutical compositions comprising a compound of the present invention as an active ingredient in admixture with a pharmaceutically acceptable non-toxic carrier. As mentioned above, such compositions can be prepared for parenteral (subcutaneous, intramuscular or intravenous) administration, particularly in the form of liquid solutions or suspensions; for oral or buccal administration, particularly in the form of tablets or capsules; for pulmonary or intranasal administration, particularly in the form of powders, nasal drops or aerosols; and for rectal or transdermal administration.

The compositions of the present invention can conveniently be administered in unit dosage form and can be prepared by any of the methods well-known in the pharmaceutical art, for example, as described in *Remington's Pharmaceutical Sciences*, 17th ed., Mack Publishing Company, Easton, Pa. (1985). Formulations for parenteral administration can contain as excipients sterile water or saline, alkylene glycols such as propylene glycol, polyalkylene glycols such as polyethylene glycol, oils of vegetable origin, hydrogenated naphthalenes and the like. Formulations for nasal administration can be solid and can contain excipients, for example, lactose or dextran, or can be aqueous or oily solutions for use in the form of nasal drops or metered spray. For buccal administration typical excipients include sugars, calcium stearate, magnesium stearate, pregelatinated starch, and the like.

Orally administrable compositions can comprise one or more physiologically compatible carriers and/or excipients and can be in solid or liquid form. Tablets and capsules can be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions can contain conventional additives such as suspending agents, for example sorbitol syrup, methyl cellulose, sugar syrup, gelatin, carboxymethylcellulose, or edible fats; emulsifying agents such as lecithin, or acacia; vegetable oils such as almond oil, coconut oil, cod liver oil;, or peanut oil; preservatives such as butylated hydroxyanisole (BHA) and butylated hydroxytoluene (BHT). Liquid compositions can be encapsulated in, for example, gelatin to provide a unit dosage form.

Preferred solid oral dosage forms include tablets, two-piece hard shell capsules and soft elastic gelatin (SEG) capsules. SEG capsules are of particular interest because they provide distinct advantages over the other two forms (see Seager, H., "Soft gelatin capsules: a solution to many tableting problems"; *Pharmaceutical Technology*, 9, (1985). Some of the advantages of using SEG capsules are: a) dose-content uniformity is optimized in SEG capsules because the drug is dissolved or dispersed in a liquid that can be dosed into the capsules accurately, b) drugs formulated as SEG capsules show good bioavailability because the drug is dissolved, solubilized or dispersed in an aqueous-miscible or oily liquid and therefore when released in the body the solutions dissolve or are emulsified to produce drug dispersions of high surface area, and c) degradation of drugs that are sensitive to oxidation during long-term storage is prevented because the dry shell of soft gelatin provides a barrier against the diffusion of oxygen.

The dry shell formulation typically comprises of about 40% to 60% concentration of gelatin, about a 20% to 30% concentration of plasticizer (such as glycerin, sorbitol or propylene glycol) and about a 30 to 40% concentration of water. Other materials such as preservatives, dyes, opacifiers and flavours also can be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

The following examples are given to enable those skilled in the art to more clearly understand and to practice the present invention. They should not be considered as limiting the scope of the invention, but merely as being illustrative and representative thereof.

EXAMPLES

The following examples are offered to illustrate, but not to limit the claimed invention.

Example 1

This example illustrate a method for producing [1R-(1α (E),3aβ,7aα)]-Octahydro-7a-methyl-1-[5,5,5-trifluoro-4-hydroxy-4-(trifluoromethyl)-2-pentynyl]cyclopropyl]-4H-inden4-ol.

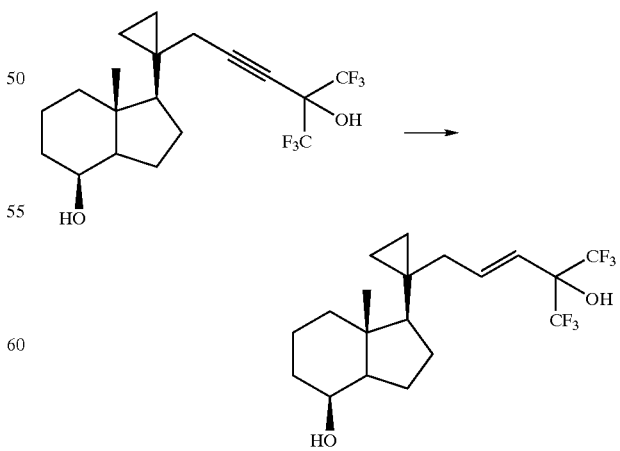

To a stirred, chilled (5° C.) suspension of LiAlH$_4$ (237.2 mg; 6.25 mmol) in anhyd. THF (6.0 ml) was added powdered NaOMe (338 mg, 6.25 mmol). The mixture was stirred under Ar at 5° C. for 15 min, treated with a solution of [1R-(1α, 3aβ,4α,7aα)]-octahydro-7a-methyl-1-[1-[5,5,5-trifluoro-4-hydroxy-4-(trifluoromethyl)-2-pentynyl] cyclopropyl]-4H-inden-4-ol (500 mg, 1.25 mmol) in anhyd THF (6.0 ml), and then boiled under reflux for 2.5 h. After cooling, the mixture was diluted with Et₂O (25 ml), quenched by the drop-wise addition of water (2.0 ml) and 2 M NaOH (2.0 ml), and stirred at room temperature for 30 min. MgSO₄ (5 g) was added, and after an additional 30 min of stirring, the mixture was diluted with Et₂O (25 ml) and filtered over Celite (15 g), which was washed with EtOAc (3×20 ml). Evaporation gave a gum (508 mg), which was purified by flash chromatography (50 g of silica gel, 3.5 cm diameter column, 30% EtOAc in hexanes), taking 20-ml fractions. Evaporation of fractions 7–12 gave colorless crystals (486 mg), which were triturated with hexane and collected by filtration to give the title compound (442 mg, 88%): mp 122–123 ° C.; $[\alpha]_D$+42.1° (EtOH, c=0.80); IR 3540, 1602, 965 cm$^{-1}$; $^1$H NMR δ0.05 (1H, m), 0.27 (1H, m), 0.34 (1H, m), 0.74 (1H, m), 0.98 (1H, m), 1.00 (3 H, s), 1.17–1.25 (2 H, m), 1.35–1.60 (6 H, m), 1.65 (1H, dd, J=12, 5), 1.75–1.87(3 H, m), 2.02 (1H, d, J=11), 2.78 (1H, dd, J=14, 8.5), 2.92 (1H, s, OH), 405 (1H, br s), H, br s), 5.59 (1H, d, J=16), 6.30 (1H, ddd, J=16, 8.5, 6); MS m/z :400 (M⁺, 10). Anal. Calcd for $C_{19}H_{26}F_6O_2$: C, 56.99; H, 6.55; F, 28.47. Found: C, 56.87; H, 6.33; F, 28.69.

Example 2

This example illustrate a method for producing, [1R-(1α(E),3aβ,7aα)]]Octahydro-7a-methyl- 1-[1-[1-[5,5,5-trifluoro-4-hydroxy-4-(trifluoromethyl)-2-pentynyl] cyclopropyl]-4H-inden-4-one.

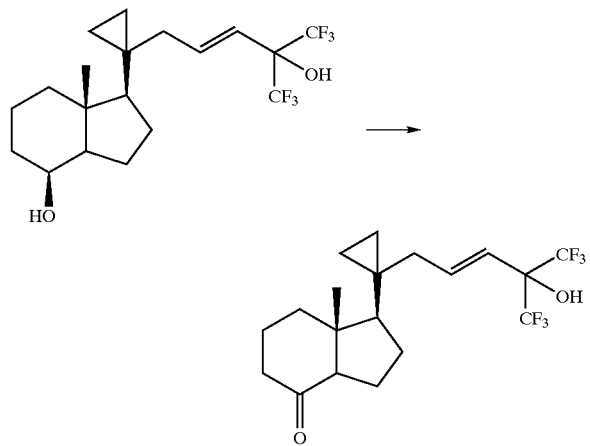

To a stirred solution of [1R-(1α(E),3aβ,4α,7aα)]] octahydro-7a-methyl-1-[5,5,5-trifluoro-4-hydroxy-4-(trifluoromethyl)-2-pentynyl]cyclopropyl]-4H-inden-4-ol (400 mg, 1.00 mmol) in CH₂Cl₂ (8.0 ml) was added pulverized pyridinium dichromate (1.25 g, 3.3 mmol). The mixture was stirred at room temperature for 4.5 h, diluted with diisopropyl ether (15 ml), and worked up to give 395 mg of a colorless gum. Flash chromatography (50 g of silica gel, 3.5 cm diameter column, 30% EtOAc in hexanes), collecting 20-ml fractions, gave after evaporation of fractions 7–12, the title compound (376 mg, 94%) as colorless crystals: mp 79–80° C.; $[\alpha]_D$+6.9° (EtOH, c=1.00); IR 3334, 1704, 964 cm$^{-1}$; $^1$H NMR δ 0.14 (1H, m), 0.33 (1H, m), 0.69 (1H, m), 0.70 (3 H, s), 1.46–1.80 (5 H, m), 1.91–2.30 (6 H, m), 2.44 (1H, dd, J=11, 6), 2.74 (1H, dd, J=15,8.5), 2.98 (1H, s, OH), 5.62 (1H, d, J=15), 6.33 (1H, dd, J=15, 8.5, 6); MS m/z 398 (M⁺, 20) Anal. Calcd for $C_{19}H_{24}F_6O_2$: C, 57.28. H, 6.07; F, 28.61. Found: C, 57.19; H, 6.25; F, 28.71.

Example 3

This example illustrates a method for producing [1R-[1α (E),3aβ,7aα)]]-Octahydro-7a-methyl-1-[1-[5,5,5-trifluoro-4- trifluoromethyl)-4-[(trimethylsilyl)oxy]-2-pentynyl]cyclopropyl]-4H-inden-4-one.

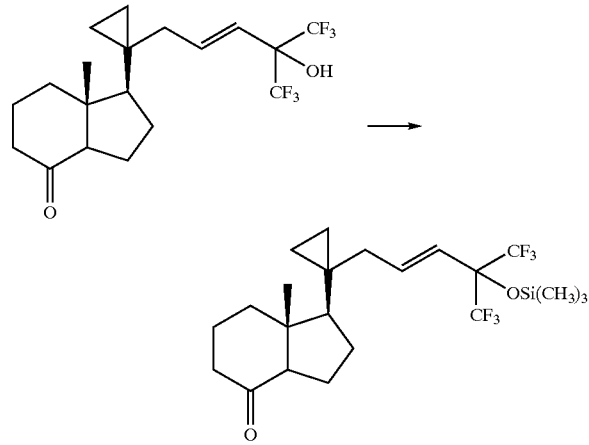

A stirred solution of [1R-(1α)(E),3aβ, 7aα)]]-octahydro-7a-methyl-1-[1-[5,5,5-trifluoro-4-hydroxy-4-trifluoromethyl)-2-pentynyl]cyclopropyl]-4H-inden-4-one (165 mg, 0.41 mmol) in anhyd CH₂Cl₂ (5 ml) was reacted with 1-(trimethylsilyl)imidazole (0.5 ml, 3.4 mmol) during 5 h to give after work up crude title compound (193 mg,). Flash chromatography (25 g of silica gel, 20% EtOAc in hexanes) gave the title compound (161 mg, 83%) as an oil: $[\alpha]_{D+}$3.4 ° CHCl₃, c=1.0); IR 1706 cm$^{-1}$; $^1$H NMR δ 0.13 (1H, m), 0.22 (9H, s), 0.32 (1H, m), 0.67 (1H, m), 0.70 (3H, s), 1.10 (1H, m), 1.50–2.40 (11H, m),2.44 (1H, dd, J=11, 6), 2.68 (1H, dd, J=16,8.5), 5.57 (1H, d, J=16), 6.16 (1H, ddd, J=16, 8.5, 6); MS m/z 470 (M⁺, 33). Anal. Calcd for $C_{22}H_{32}F_6O_2Si$: C, 56.15; H, 6.85; F, 24.22. Found: C, 56.42; H, 6.63; F, 24.37.

Example 4

This example illustrates a method for producing 3-desoxy-1,25-dihydroxy-20-methyl-23-(E)-ene-26,27-hexafluoro-21,28-cyclochole-calciferol.

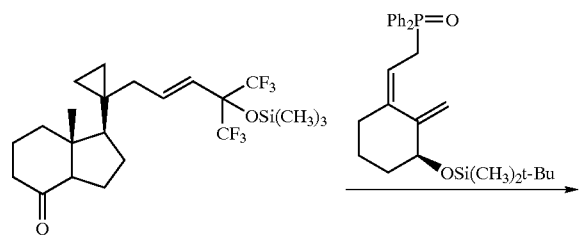

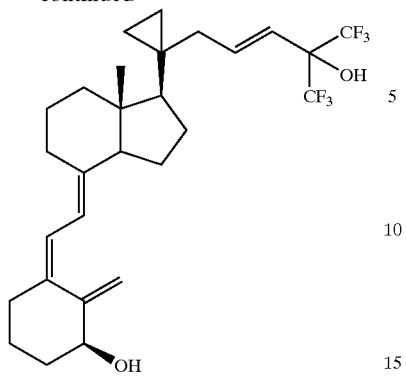

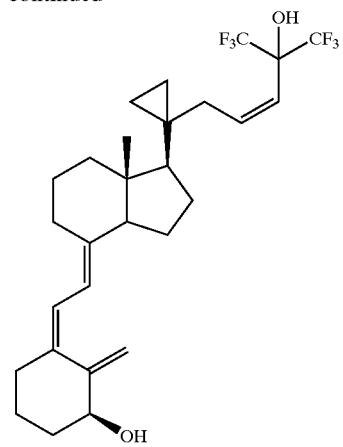

Horner reagent [R-(Z)]-[2-[3-[[(1,1-dimethylethyl)-dimethyl-silyl]oxy]-2-methylenecyclohexylidene]ethyl] diphenylphosphine oxide (395 mg, 0.872 mmol) in anhydrous THF (5.0 ml) was deprotonated with a 1.6 M solution of n-BuLi in hexanes (0.55 ml, 0.88 mmol) at −78 °C. and after 8 min reacted with ketone [1S-[1α(E),3aβ,7aβ]] octahydro-7a-methyl-1-[1-[5,5,5-trifluoro-4-(trifluoromethyl)-4-[trimethylsilyl)oxy-2-pentenyl]cyclopropyl]-4H-inden-4-one (170 mg, 0.361 mmol) in anhyd THF (2.0 ml) during 3 h and worked up. Flash chromatography (45 g of silica gel, 20% EtOAc in hexanes) gave a gum (215 mg). This was dissolved in THF (3 ml), treated with 1.0 M solution of n-Bu$_4$N$^+$F in THF (2.8 ml) and stirred for 19 h. Work up followed by flash chromatography (40 g silica gel, 40% EtOAc in hexanes) gave a gum, which was dissolved in HCO$_2$Me (5.0 ml), filtered through a 0.45 μm filter and evaporated. High vacuum drying (3 h) gave title compound (144 mg) as a colorless foam: $[\alpha]_D$ 4.0° (MeOH, c=0.35); UV $\lambda_{max}$ 265 (ε=15,837), 211 (ε=14,458) nm; IR 3598, 1651 cm$^{-1}$; $^1$H NMR δ 0.11 (1H, m), 0.29 (2H, m), 0.60 (3H, s), 0.61 (1H, m), 1.10 (1H, m), 1.21–1.35 (1H, m), 1.50 (6H, m), 1.70 (2 H, m), 1.90 (2 H, m), 2.00 (3 H, m), 2.30 (2 H, m), 2.60 (1H, J=12), 2.85 (2 H, m), 2.90 (1H, s), 4.22 (1H, s), 4.42 (1H, s), 4.99 (1H, s), 5.32 (1H, s), 5.42 (1 H, d, J=12), 5.99 (1H, d, J=11), 6.10 (1H, ddd, J=12, 7, 6), 6.36(1H, d, J=11); MS (FAB) m/z 535 (M$^+$+H).

Example 5

This example illustrates a method for producing 3-desoxy-1,25-dihydroxy-20-methyl-23-(Z)-ene-26,27-hexafluoro-21,28-cyclocholecalciferol.

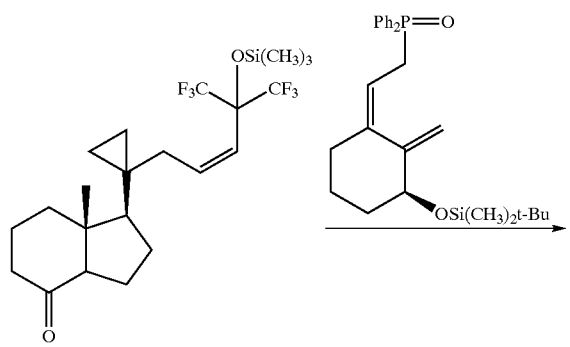

Horner reagent [R-(Z)]-2-[3-[[(1,1-dimethylethyl)-dimethylsilyl]oxy]-2-methylenecyclohexylidene]ethyl] diphenylphosphineoxide (236 mg, 0.5 mmol) in THF (3.0 ml) was treated with a 1.6 M solution of n-BuLi in hexanes (0.32 ml, 0.512 mmol). After 8 min, ketone [1 S-[1α(Z), 3aβ, 7aα]]octahydro-7a-methyl-1-[1-[5,5,5-trifluoro-4-[(trimethylsilyl)oxy]-2-pentenyl]cyclopropyl-4H-inden-4-one (117.5 mg, 0.25 mmol) in THF (2.0 ml) was added and stirring continued for 2.5 h. Work up gave a gum, which was purified by flash chromatography (40 g of silica gel, 20% EtOAc in hexanes) to give a gum (120 mg). This was dissolved in THF (2.0 ml), treated with a 1 M solution of n-Bu$_4$N$^+$F in THF (2.0 ml) and stirred at room temperature for 20 h, and worked up. Flash chromatography (40 g of silica gel, 40% EtOAc in hexanes) gave title compound (29 mg) as a colorless foam: $[\alpha]_D$ −41° (MeOH, c=0.14); IR 3569 cm$^{-1}$; UV $\lambda_{max}$ 214 (10,968), 219 (12,931), 259 (12,818) nm; $^1$H NMR δ 0.02 (1H, m), 0.32 (2 H, m), 0.60 (1H, m), 0.61 (3 H, s), 1.1–1.7 (11H, m), 1.85 (2 H, m), 2.0 (3 H, m), 2.2 (3 H, m), 2.85 (3 H, m), 4.12 (1H, br s), 4.90 (1H, s), 5.30 (1H, s,), 5.40 (1H, d, J=12.8), 6.0 (1H, d, J=11), 6.12 (1H, dd, J=12.8, 6.8), 6.29 (1H, d, J=11), 6.12 (1H dd, J=12.8, 6.8), 6.29 (1H, d, J=11); MS m/z 518 (M$^+$, 22).

Example 6

This example illustrates a method for producing 3-desoxy-1,25-dihydroxy-20-methyl-23-yne-21,28-cyclocholecalciferol.

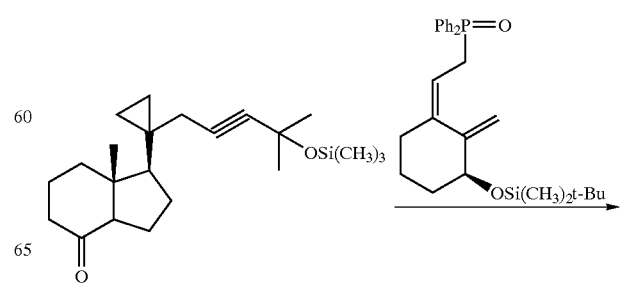

25

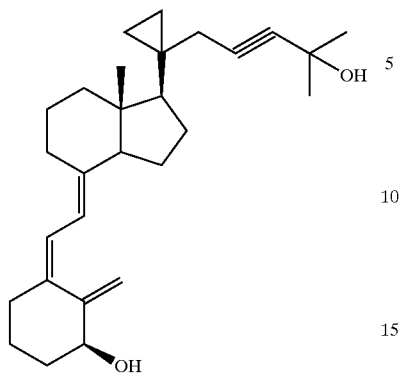

Horner reagent [R-(Z)]-[2-[3-[[(1,1-dimethylethyl)dimethylsilyl]oxy]-2-methylenecyclo-hexylidene]ethyl]diphenylphosphine oxide (375 mg, 0.828) in THF (5.0 ml) was treated with 1.6 M solution of n-BuLi in hexanes (0.51 ml, 0.81 mmol). After 8 min, [1R-(1α, 3aβ,7aα)]-Octahydro-7a-methyl-1-[4-methyl-4-[(trimethylsilyl)oxy]-2-pentynyl]cyclopropyl]-4H-inden-4-one (180 mg 0.50 mmol) in THF (4.0 ml) was added and the mixture worked up after 3.5 h. Flash chromatography (45 g of silica gel, 7% EtOAc in hexanes) gave a syrup (273 mg), which was dissolved in THF (3.3 ml) and stirred with a 1.0 M solution of n-Bu$_4$N$^+$F$^-$ in THF (3.3 ml) for 28 h, and worked up. Flash chromato-graphy (45 g silica gel, 40% EtOAc in hexanes) gave title compound (114 mg) as a colorless foam: [α]$_D$-70.32° (EtOH, c=0.539); UV λ$_{max}$, 215 (ε=13,326), 262 (ε=17,661) nm; IR 3601 cm$^{-1}$; $^1$NMR δ 0.28 (2H, m), 0.41 (1H, m), 0.59(1H, m), 0.60 (3H, s), 1.10 (1H, m), 1.50 (6H, s), 1.55–2.0 (18H, m), 209 (1H, d, J=17), 2.22 (2H, m), 2.60 (1H, d, J=17), 2.80 (1H, d, J=11), 4.11 (1H, br, s) 2.09 (1H, s), 5.30 (1H, s), 5.99 (1H, d, J=11), 6.27 (1H, d, J=11); MS m/z 408.3 (M$^+$, 60).

Example 7

This example illustrates a method for producing 3-desoxy-1,25-dihydroxy-20-methyl-23-yne-26,27-hexafluoro-21,28-cyclocholecalciferol.

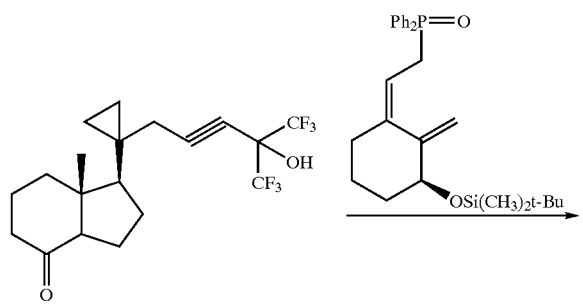

26

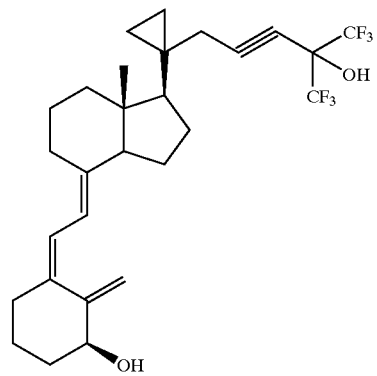

Horner reagent [R-(Z)]-[2-[3-[[(1,1-dimethylethyl)-dimethylsilyl]oxy]-2-methylenecyclohexylidene]ethyl] diphenylphosphineoxide (350 mg, 0.773 mmol) in THF (5.0 ml) was deprotonated with 1.6 M n-BuLi in hexanes (0.49 ml, 0.784 mmol) at −78° C. and after 8 min reacted with ketone [1S-1α,3aβ,7a α)]octahydro-7a-methyl-1-[1-[5,5,5-trifluoro-4-hydroxy-4-(trifluoromethyl)-2-pentynyl]cyclopropyl]-4H-inden-4-one (158 mg, 0.40 mmol) during 3.0 h. Flash chromatography of the crude product (45 g silica gel, 20% EtOAc in hexanes) followed by desilylation during 18 h at room temperature with a 1 M solution of n-Bu$_4$N$^+$F$^-$ in THF (1.8 ml) and flash chromato-graphic purification (45 g silica gel, 40% EtOAc in hexanes) gave title compound (117 mg) as a colorless foam: [α]$_D$- 58.3° (EtOH, c=0.456); UV λ$_{max}$ 214 (ε=12,900), 260 (ε=15,701) nm; $^1$H NMR δ 0.29 (1H, m), 0.35 (1H, m), 0.37 (1H, m) 0.59 (3 H, s), 0.64 (1H, m), 1.4–1.90 (12 H, m) 2.00 (4 H, m), 2.18 (1H, d, J=17), 2.25 (2 H, m), 2.72 (1H, d, J=17),2.81 (1H, m), 3.34 (1H, s, OH), 4.12 (1H, br s),4.92 (1H, s), 5.28 (1H, s), 5.98 (1H, d, J=11), 6.27 (1H, d, J=11); MS m/z 516.2 (M$^+$, 90).

Example 8

This example illustrates a method for producing 3-desoxy- 1,25-dihydroxy-20-methyl-21,28-cyclocholecalciferol.

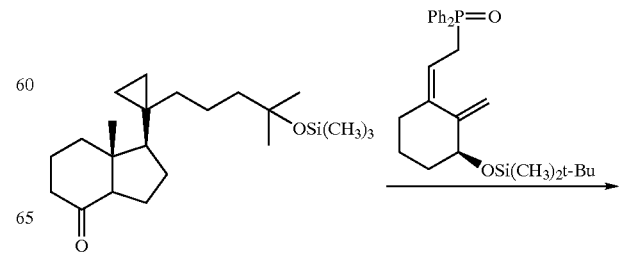

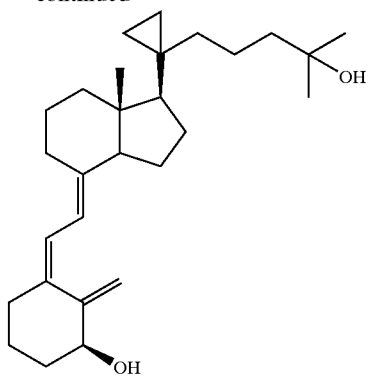

A magnetically stirred 25 ml, 3-neck round bottom flask equipped with a thermometer, a rubber septum on the side and a Claisen adapter containing a nitrogen sweep and rubber septum at the center, was charged with 0.564 gr (1,246 mmol) of [R-(Z)]-2-[3-[[(1,1-dimethylethyl)-dimethylsilyl]oxy]-2-methylenecyclohexylidene]ethyl] diphenyl-phosphine oxide. This material was dried under high vacuum, and was added 5 ml tetrahydrofuran; the solution was stirred and cooled to −70° C., and 0.78 ml (1.246 mmol) of 1.6 M BuLi in hexane was added. (The red color persisted after the initial 0.16 ml was added). The solution was stirred at −70° C. for 10 min, and then a solution of 0.2904 gr (0.796 mmol) of [1S-(1α, 3aβ, 7aα)] octahydro-7a-methyl-1-[1-[4-methyl-4-oxy]-2-pentanyl-cyclo-propyl]-4H-inden-4-one dissolved in 8 m tetrahydrofuran was added dropwise. When the reaction was virtually complete (TLC, 1:9 ethyl acetate-hexane), the mixture was allowed to warm to −30° C., then 12 ml of pH7 phosphate buffer (139.4 gr of dipotassium phosphate in 400 ml of water plus 10 ml of 2M phosphoric acid) was added dropwise through the center port. The mixture was stirred for 5 min, then transferred to a separatory funnel with the aid of 35 ml of hexane. The aqueous phase was re-extracted with 30 ml of hexane. The two hexane layer were combined, washed with 20 ml of brine, dried by passage through a plug of sodium sulfate, then evaporated to a colorless syrup. This material was taken in hexane. White solids were present so that hexane suspension had to be filtered through a flash column 25×120 mm. After fraction #2 (20 ml each) the mobile phase was changed to 1:79 ethylacetate-hexane. Fractions 11–18 (according to TLC in 1:19 ethyl acetate-hexane) were pooled and evaporated. It gave 0.4202 gr (88.1%) of silylated title compound.

A 100 ml brown round-bottom flask was charged with 0.4202 gr of silylated title compound. To this material was added 5 ml tetrahydrofuran and 3.5 ml of a 1 M solution of tetrabutylammonium fluoride in tetrahydrofuran and stirred at room temperature for 17 hrs. TLC (1:1 ethyl acetate-hexane and ethyl acetate) showed one major spot. The reaction mixture was then diluted with 13 ml of brine, stirred for 15 min, then transferred to a separatory funnel with aid of 40 ml ethyl acetate. The aqueous layer was re-extracted with 20 ml of ethyl acetate. Both organic layers were combined and washed with 5×35 ml water and once with brine, then passed through a plug of sodium sulfate and evaporated to a crystalline, white residue, 0.3523 gr. This material was chromatographed on a 25×110 mm column using 1:1 ethyl acetate-hexane as mobile phase. Fractions 3–4, already crystallizing in the tubes. The suspension so obtained was concentrated to a volume of ca 5 ml, diluted with hexane and concentrated, and filtered to give crystalline title compound 0.2567 gr. $[α]_D^{25}$-59.1° (c 0.325, EtOH). UVλ$_{max}$ (MeOH): 214, 262; λ$_{sh}$ 222 nm. Anal. Calcd for $C_{28}H_{44}O$: C, 81.50; H, 10.75; 0, 7.75. Found: C, 81.43; H, 10.69; 0, 7.48.

Example 9

This example illustrate a method for synthesizing 3-desoxy-1α-acetoxy-25-hydroxy-20-cyclopropyl-23E-ene-26,27-hexafluoro-cholecalciferol.

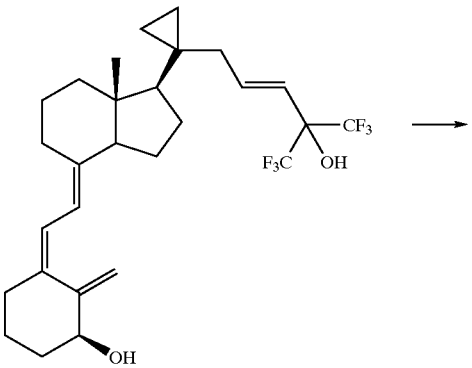

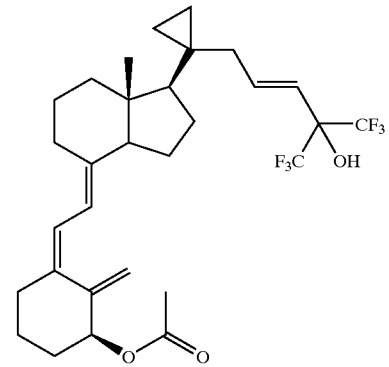

A 25-mL round bottom flask was charged with 0.1702 g of 3-desoxy-1α,25-dihydroxy-20-cyclopropyl-23E-ene-26,27-hexafluoro-cholecalciferol and 2.85 g of pyridine. The solution was stirred and cooled in an ice bath, then 0.5 mL of acetic anhydride was added and stirring in the ice bath continued for one hour. At that time the solution was placed in the refrigerator overnight. The flask was returned to the ice-bath and 0.2 mL of acetic anhydride was added. After 6 hours the solution was diluted with 10 mL of ethyl acetate and, while still immersed in the ice bath, 2 mL of water was added. The mixture was stirred for 5 min, then transferred to a separatory funnel with the aid of 20 mL of water and 20 mL of 1:4 ethyl acetate—hexane. The aqueous phase was re-extracted with 10 mL of 1:4 ethyl acetate-hexane. TLC in 1:2 ethyl acetate-hexane showed no product in this second extract. Thus, the original extract was washed with 4×20 mL of water, 10 mL of brine and then passed through a plug of sodium sulfate and evaporated. The residue was taken up in 1:4 ethyl acetate-hexane and flash chromatographed on a 15×150 mm column using 1:4 ethyl acetate-hexane as mobile phase and taking 10 mL fractions. The bulk of the major product (0.1050 g) was contained in fraction 3. Fraction 3 still contained a trace of the faster running material observed in fraction 2. As an attempt was made to dissolve the residue in 1:6 ethyl acetate-hexane crystallization commenced. Thus, a small quantity of pentane was added and the mixture allowed to crystallize in the refrigerator. The mother liquor was withdrawn, and evaporated, 0.0068 g. The crystals were rinsed once with pentane, dried to give 0.0899 g of the title compound.

$[\alpha]_D$-30.8° (0.54%, methanol), NMR (CDCl3): δ 2.07 (OAc), Anal. Calcd C 64.27, H 6.83 Found: C 64.63, H 6.93; C 64.52, H 6.94 UV max, nm (absorbance) 121 (0.3639), 250 (0.4591), 262 (4486), 244 sh (0.4482).

Example 10

This example illustrate a method for synthesizing 3-desoxy-1α,25-diacetoxy-20-cyclopropyl-23E-ene-26,27-hexafluoro-cholecalciferol.

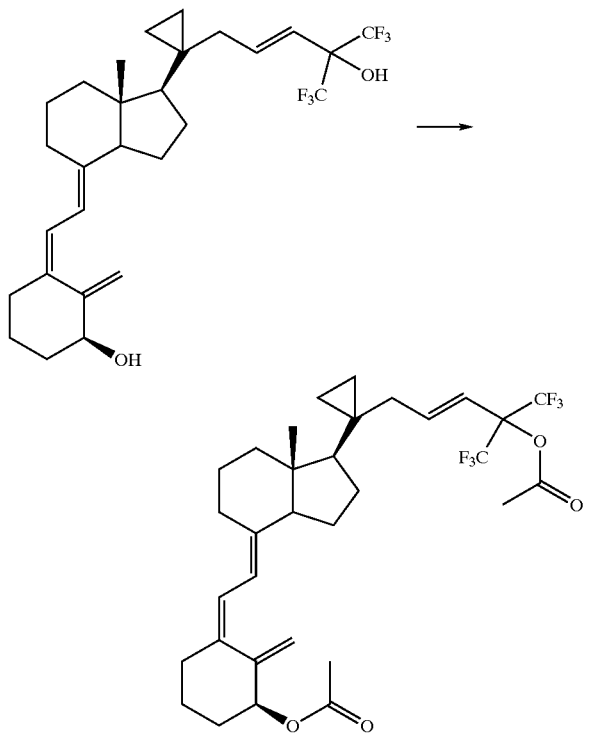

A 25-mL round bottom flask, equipped with magnetic stirred and Claisen adapter containing a nitrogen sweep and stopper, was charged with 0.315 g (0.6 mmol) of 3-desoxy-1α, 25-dihydroxy-20-cyclopropyl-26,27-hexafluoro-cholecalciferol, 60 mg of dimethylaminopyridine, 5 mL of pyridine. The pyridine was added while the flask was immersed in an ice bath. After 10 min, 1.0 mL of acetic anhydride was added dropwise and stirring in the ice bath continued. After 1 hour starting material was virtually undetectable. After two hours, the solution was diluted with 10 mL of ethyl acetate and, while still immersed in the ice bath, 10 min later, 2 mL of water was added dropwise. The mixture was stirred for 10 min, then transferred to a separatory funnel with the aid of 20 mL of water and 20 mL of 1:4 ethyl acetate—hexane. The aqueous phase was re-extracted with 10mL of 1.4 ethyl acetate—hexane. TLC in 1:2 ethyl acetate—hexane showed no product in this second extract. Thus, the original extract was washed with 4×20 mL of water, 20 mL of brine and then passed trough a plug of sodium sulfate and evaporated. The residue was taken up in 1:6 ethyl acetate—hexane and flash chromatographed on a 25×150 mm column using 1:6 ethyl acetate—hexane as mobile phase and taking 20-ml fractions. Pure material was contained in fraction 3, fraction 4–6 contained the product contaminated with slower-moving materials (TLC 1:2). Thus, fractions 4–6 were combined and the residue re-chromatographed on a 15×150 mm column using 1:9 ethyl acetate—hexane as mobile phase and taking 20 mL fractions. Fractions 2 and 3 contained the bulk of the product in pure form. These fractions were added to fraction 3 of the first chromatogram, then evaporated. The residue was taken up in 1:9, filtered and concentrated, diluted with pentane and refrigerated. The mother liquor was withdrawn and the crystals rinsed with pentane, then dried at hivac for 2 h, to give 0.190 g of the title compound.

NMR (CDCl$_3$): δ2.08 and 2.20 (2 OAc), $[\alpha]_D$- 110.3, 0.59% (methanol), MA 192020: found C, 63.99; H, 6.62; calcd C, 63.78; H, 6.69, UV max (Absorbance) 212 (0.3573), 251 (0.4392), 261 (0.4276).

Example 11

This example illustrates a method of determining effectiveness of the compounds of the present invention for bone anabolism in the rat.

Three month old rats are ovariectomized (Ovx) and administered either 1,25-dihydroxy vitamin D$_3$ or one of the compounds of the present invention once a day by mouth starting at 3 weeks post-ovariectomy and continuing until final sacrifice at 6 weeks post-ovariectomy. Control groups, both sham (rats that were not ovariectomized) and Ovx, receive vehicle only. Blood and urine samples are collected twice, at 4 weeks post-ovariectomy and again at the 6 week mark and the amount of serum and urine calcium is determined. The final femoral calcium is determined upon sacrifice 6 weeks post-ovariectomy.

The bone mineral density of the right femur is determined by using a High Resolution Software Package on a QDR-1000W Bone Densitometer™ (Hologic, Walthan, Mass.). The animals are scanned by placing them on a scanning block in a supine position such that the right leg was perpendicular to the main body and the tibia was perpendicular to the femur.

Example 12

This example illustrates a method for determining comparative in vivo efficacy of Compounds of the present invention and 1,25-(OH)$_2$Vitamin D$_3$.

Comparison of the efficacy of compounds of the present invention to that of 1,25-dihydroxy vitamin D$_3$, can be made using the standard animal model for post menopausal osteopenia, the rat ovariectomy model. Three month old rats were ovariectomized, and then treated for 8 weeks beginning 1 week post OVX. Drugs were administered once/day orally in miglyol (medium chain triglyceride) vehicle. Blood and urine samples were collected at the 3 wk and 6 wk time point, and bone mineral density (BMD) was determined in vivo at 6 wk using Dual Energy X-ray Absorptiometry (Hologic QDR-4500™ Bone Scanner). At 8 weeks, the animals were sacrificed, and the lumbar vertebrae and femur bones removed for ex vivo BMD determination (Lunar PixiMus™ Bone Scanner) and biomechanical testing for strength. Data for each compound are then determined for the highest safe doses. The highest safe dose is defined as that which does not produce hypercalcemia as defined by serum calcium levels greater than 10.0 mg/dl.

The foregoing invention has been described in some detail by way of illustration and example, for the purposes of clarity and understanding. It will be obvious to one of ordinary skill in the art that changes and modifications may be practiced within the scope of the appended claims. Therefore, it is to be understood that the above description is intended to be illustrative and not restrictive. The scope of the invention should, therefore, be determined with reference to the following appended claims, along with the full scope of equivalents to which such claims are entitled.

The patents, patent applications and publications cited in this application are hereby incorporated by reference in their entirety for all purposes to the same extent as if each individual patent, patent application or publication were so individually denoted.

What is claimed is:

1. A 3-desoxy vitamin $D_3$ compound of the formula:

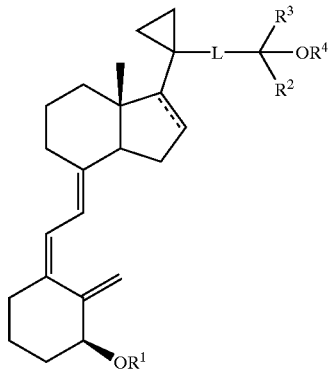

I or a salt thereof, wherein dotted line is optionally a double bond;

L is a linker selected from the group consisting of:
—$CH_2$—$CH_2$—$CH_2$—,
—$CH_2$—CH=CH—,
—$CH_2$—C≡C—,
—$CH_2$—$CH_2$—C(=O)—, and
—CH=CH—CH=CH—;

each of $R^2$ and $R^3$ is independently alkyl or haloalkyl; or $R^2$ and $R^3$ and together with the carbon atom to which they are attached to form a cycloalkyl; and each of $R^1$ and $R^4$ is independently hydrogen, alkyl, acyl group or other hydroxy protecting group, provided at least one of $R^1$ and $R^4$ is an acyl group.

2. The 3-desoxy vitamin $D_3$ compound according to claim 1 of the formula:

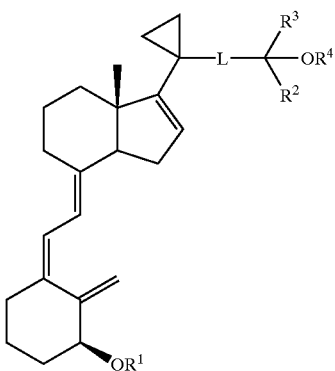

wherein
$R^1$, $R^2$, $R^3$, $R^4$ and L are those defined in claim 1.

3. The 3-desoxy vitamin $D_3$ compound according to claim 1 of the formula:

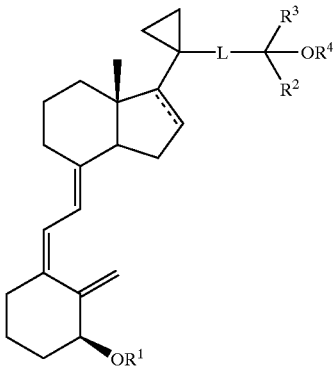

wherein
L is selected from the group consisting of:
—$CH_2$—$CH_2$—$CH_2$—;
—$CH_2$—CH=CH—;
—$CH_2$—C≡C—; and
—CH=CH—CH=CH—.

4. The 3-desoxy vitamin $D_3$ compound according to claim 3, wherein said linker L is selected from the group consisting of:
—$CH_2$—CH=CH—; and
—$CH_2$C≡C—.

5. The 3-desoxy vitamin $D_3$ compound according to claim 4, wherein $R^1$ is an acyl group.

6. The 3-desoxy vitamin $D_3$ compound according to claim 5, wherein $R^4$ is an acyl group.

7. The 3-desoxy vitamin $D_3$ compound according to claim 5, wherein each of $R^2$ and $R^3$ is independently selected from the group consisting of alkyl and haloalkyl.

8. The 3-desoxy vitamin $D_3$ compound according to claim 5, wherein $R^2$ and $R^3$ are trifluoromethyl.

9. A method for treating a bone related disease in a patient comprising administering a compound of claim 1 to the patient.

10. A method for treating hyperparathyroidism in a patient comprising administering a compound of claim 1 to the patient.

11. The method of claim 10, wherein the disease is secondary hyperparathyroidism.

12. The method of claim 10, wherein the disease is renal osteodystrophy.

13. The method of claim 9, wherein the disease is osteoporosis.

14. A method for producing a vitamin $D_3$ compound of the formula:

comprising:
(a) contacting a ketone of the formula:

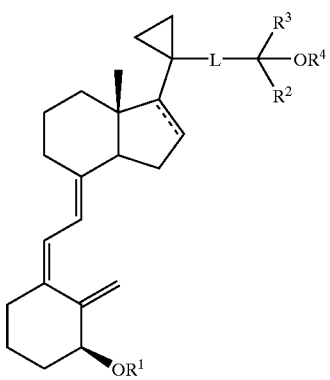

I with a phosphine oxide compound of the formula:

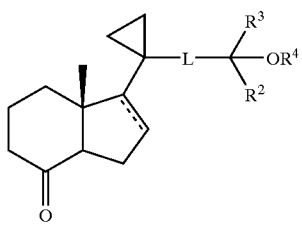

II

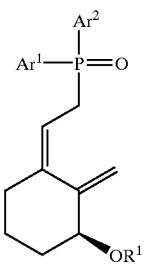

III under conditions sufficient to produce said compound of Formula I, wherein
each of $Ar^1$ and $Ar^2$ is independently optionally substituted aryl;
dotted line is optionally a double bond;
L is a linker selected from the group consisting of:
—$CH_2$—$CH_2$—$CH_2$—,
—$CH_2$—CH=CH—,
—$CH_2$—C≡C—,
—$CH_2$—$CH_2$—C(=O)—, and
—CH=CH—CH=CH—;
each of $R^2$ and $R^3$ is independently alkyl or haloalkyl; or $R^2$ and $R^3$ and together with the carbon atom to which they are attached to form a cycloalkyl; and
each of $R^1$ and $R^4$ is independently alkyl, an acyl group or a hydroxy protecting group, and
(b) when neither $R^1$ nor $R^4$ is an acyl group, acylating the compound of Formula I with an acylating agent under conditions sufficient to produce the Compound of Formula I where at least one of $R^1$ and $R^4$ is an acyl group.

15. The method of claim 14, wherein $R^1$ and $R^4$ are hydroxy protecting groups.

16. The method of claim 15, wherein said acylating step (b) comprises:

(i) removing the hydroxy groups by contacting the resulting compound of said step (a) with a hydroxy protecting group removing compound under conditions sufficient to produce a 1-hydroxy-3-desoxy vitamin $D_3$ analog of the formula:

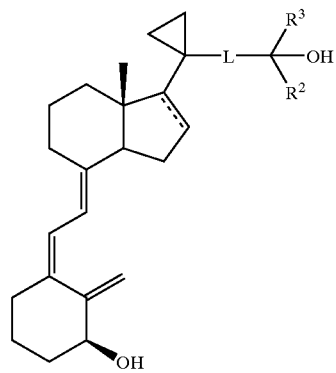

and (ii) contacting the 1-hydroxy-3-desoxy vitamin $D_3$ analog with an acylating agent under conditions sufficient to produce a 3-desoxy vitamin $D_3$ compound of the Formula:

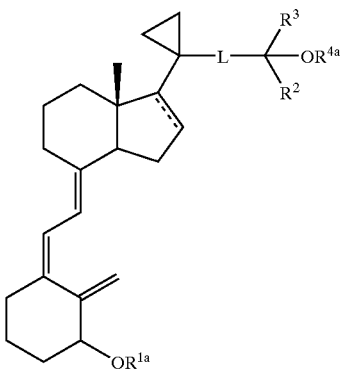

wherein $R^{1a}$ is an acyl group and $R^{4a}$ is hydrogen or an acyl group.

17. The method of claim 16, wherein $R^{4a}$ is an acyl group.

18. The method of claim 14, wherein $Ar^1$ and $Ar^2$ are phenyl.

19. A pharmaceutical composition comprising a compound of claim 1 and a pharmaceutically acceptable excipient.

* * * * *